US008560077B2

(12) United States Patent
Feinstein

(10) Patent No.: US 8,560,077 B2
(45) Date of Patent: Oct. 15, 2013

(54) UNIVERSAL MUSCULOSKELETAL REHAB DEVICE (BRACE, SLEEVE, OR PAD) FOR ELECTRICAL TREATMENT MODALITIES AND BIOFEEDBACK RESPONSE MONITORING

(75) Inventor: Peter A. Feinstein, Shavertown, PA (US)

(73) Assignee: Feinstein Patents LLC, Shavertown, PA (US)

(*) Notice: Subject to any disclaimer, the term of this patent is extended or adjusted under 35 U.S.C. 154(b) by 20 days.

(21) Appl. No.: 13/398,039

(22) Filed: Feb. 16, 2012

(65) Prior Publication Data

US 2013/0085317 A1    Apr. 4, 2013

Related U.S. Application Data

(60) Provisional application No. 61/543,076, filed on Oct. 4, 2011.

(51) Int. Cl.
*A61N 1/04* (2006.01)

(52) U.S. Cl.
USPC .............................. 607/48; 600/14

(58) Field of Classification Search
USPC ............................... 607/48; 600/14
See application file for complete search history.

(56) References Cited

U.S. PATENT DOCUMENTS

| 4,569,352 | A |   | 2/1986  | Petrofsky et al. |
|-----------|---|---|---------|------------------|
| 4,760,850 | A |   | 8/1988  | Phillips et al.  |
| 5,014,705 | A | * | 5/1991  | Graupe et al. ............ 607/49 |
| 5,121,747 | A |   | 6/1992  | Andrews          |
| 5,947,913 | A |   | 9/1999  | Palumbo          |
| 6,132,362 | A | * | 10/2000 | Tepper et al. ............ 600/14 |
| 7,758,527 | B2|   | 7/2010  | Gilmour et al.   |
| 7,783,348 | B2|   | 8/2010  | Gill et al.      |
| 8,070,703 | B2| * | 12/2011 | Skahan et al. ........... 602/23 |
| 2006/0206167 | A1 | | 9/2006 | Flaherty et al. |
| 2007/0038252 | A1 | | 2/2007 | Carroll |

(Continued)

FOREIGN PATENT DOCUMENTS

WO    2010064206 A1    6/2010

OTHER PUBLICATIONS

International Search Report and Written Opinion of the International Searching Authority Application No. PCT/US2012/057712 Completed: Nov. 27, 2012; Mailing Date: Jan. 9, 2013 13 pages.

*Primary Examiner* — Christopher D Koharski
*Assistant Examiner* — Michael Carey
(74) *Attorney, Agent, or Firm* — St. Onge Steward Johnston & Reens LLC

(57) ABSTRACT

A non-invasive device for assisting the treatment of any kind of musculoskeletal disorder, including but not exclusive of those of joint, limb, and spine disorders, includes a brace, sleeve, flexible pad, or any combination of the three, a plurality of electrodes disposed thereon, wherein the plurality of electrodes transmit at least three electrophysical modalities, and a stimulation control unit having interactive software to establish a controlled sequence of transmission of the at least three electrophysical modalities and communicating the controlled sequence to the electrodes. The at least three electrophysical modalities are chosen from a group consisting of neuromodulating functional electrical stimulation, transcutaneous electrical nerve stimulation, pulsed electromagnetic field stimulation, and heat therapy stimulation. The stimulation control unit also provides feedback data using the electrodes for monitoring and integration with the interactive software to analyze and assess biomechanical, neuromuscular, and neurological responses to the device.

38 Claims, 12 Drawing Sheets

(56) References Cited

U.S. PATENT DOCUMENTS

| | | |
|---|---|---|
| 2010/0082079 A1 | 4/2010 | Skahan et al. |
| 2010/0262044 A1 | 10/2010 | Siegler et al. |
| 2010/0262052 A1 | 10/2010 | Lunau et al. |
| 2010/0318009 A1* | 12/2010 | Stanley ............... 602/14 |
| 2011/0112605 A1* | 5/2011 | Fahey ............... 607/48 |
| 2011/0118805 A1* | 5/2011 | Wei et al. ............... 607/41 |
| 2011/0264002 A1* | 10/2011 | Kolen et al. ............... 600/554 |
| 2011/0288611 A1 | 11/2011 | Lunau et al. |

* cited by examiner

SIDE VIEW

LOOKING INSIDE
THE BRACE

UNIVERSAL MUSCULOSKELETAL REHAB DEVICE (BRACE, SLEEVE, OR PAD) FOR ELECTRICAL TREATMENT MODALITIES AND BIOFEEDBACK RESPONSE MONITORING

CROSS-REFERENCE TO RELATED APPLICATIONS

This patent application claims the benefit of, under Title 35, United States Code, Section 119(e), U.S. Provisional Patent Application No. 61/543,076, filed Oct. 4, 2011, the content of which is incorporated herein by reference.

FIELD OF THE INVENTION

The invention relates to a rehab device and more specifically to a flexible sleeve, flexible pad and/or an orthotic brace, applied by itself or associated with and incorporated into any of these three devices, conforming to a patient's body and being capable of providing multiple electrical treatment modalities and biomechanical analysis for non-invasive treatment of an articulating joint and any associated soft tissue injury, inflammation or pathology related to any injury, disorder, disease, or other medical disability.

BACKGROUND OF THE INVENTION

Osteoarthritis, posttraumatic arthritis, inflammatory arthritis such as rheumatoid arthritis, systemic lupus erythematosus and ankylosing spondylitis, and degenerative joint disease are all common musculoskeletal disorders that cause wear and tear on a joint. In particular, protective cartilage which cushions the bones at the joint can break down and wear away over time. When this happens, the bones rub against each other, causing pain, swelling, stiffness, and restricted movement. While osteoarthritis and other musculoskeletal disorders damage the joint, they also harm the muscles, tendons, ligaments, cartilage, nerves, and discs.

Musculoskeletal diseases can affect any person of any age, and in many cases no cure exists. But several forms of treatment can slow the progression and severity of musculoskeletal joint, limb, or spine disorders involving the bones, cartilage, tendons, ligaments, muscles, nerves, or discs, as well as relieve pain and improve joint function. One typical form of treatment of arthritis and musculoskeletal soft tissue diseases involves bracing the joint—or an area near the joint—with an orthotic device. Orthotic devices, such as a knee brace, are known to provide unloading support and strength to an injured joint. Despite providing some therapeutic benefits, knee braces are known to cause muscle atrophy as a result of immobilizing the joint. As a means to prevent this negative effect, muscle stimulating means are combined with orthotic devices and other similar devices to assist in either inhibiting or preventing harmful deterioration of muscle mass. Furthermore, an orthotic device or other rehab device with stimulating means can control pain in the muscles and rehabilitate the injured joint and soft tissues without requiring physical penetration through the skin. As an example, this advantage is particularly important to patients with knee osteoarthritis who do not wish for an invasive surgical procedure or a total knee replacement, or patients who have medical contraindications to knee replacement. Therefore, orthotic devices that can simultaneously provide transcutaneous stimulation, unloading support for weight-bearing joints, and other mechanical therapeutic benefits to any joint in general offer an attractive option for alleviating pain and facilitating the rehabilitation of arthritic joints and muscles.

Some orthotic devices use electrical currents as a form of stimulation to reduce pain and aid in muscle therapy. For example, U.S. Pat. No. 5,947,913 to Palumbo discloses a patellar stabilizing brace comprising a bracing means for applying a medial force on the patella, a generator producing neuromuscular electrical stimulation (NES), and a plurality of electrodes to transmit the electrical stimulation to a muscle mass. The generator is mounted on a sleeve that attaches to the brace using hook-and-loop VELCRO® fasteners while the electrodes are disposed along the sleeve, either penetrating it or passing beneath or above it. Thus, a patient wearing the stabilizing brace would experience periodic stimulation from the electrodes via a transcutaneous method. Further, a transcutaneous electrical nerve stimulation (TENS) unit for providing pain management can be attached to the stabilizing brace. However, without a controller, the Palumbo device lacked the capability for selectively stimulating certain muscles or implementing a programmed sequence of stimulation.

Other efforts have been made to provide an orthotic device conveying some form of stimulation to aid in the therapy of osteoarthritis. For example, U.S. Pat. No. 7,783,348 to Gill et al. discloses a portable, non-invasive device for providing therapeutic treatment to a knee joint comprising a knee cuff which in turn comprises a thermal exchange component for applying thermal therapy, a signal generator for generating a pulsed electromagnetic field (PEMF) in stimulators, and a controller for storing a treatment mode and communicating the treatment mode to the signal generator and stimulators. However, the orthotic device disclosed in Gill does not provide unloading support or strength to the knee joint and thus does not relieve pressure off the part of the knee joint that is affected by osteoarthritis, arthritides, or soft tissue pathologies. Further, no electrical stimulation is provided in order to alleviate the pain associated with the osteoarthritis.

U.S. Pat. No. 8,070,703 to Skahan et al. discloses a knee brace system comprising a substantially rigid brace structure having upper and lower supports for securing the brace to the patient's leg, liner segments attached to each support, and a plurality of electrodes attached to the liner segments which supply stimulation from an electrostimulation unit. Further, the liner segments can be removed and reattached to adjust their position in order to maintain stable contact between the electrodes and the patient's leg. Used in conjunction with the electrostimulation unit, the plurality of electrodes can provide an electrophysical modality, such as Surface Electrical Stimulation, NES, PEMF Stimulation, or TENS, to the patient's knee. However, Skahan does not provide for simultaneous or coordinated treatment of a combination of electrophysical modalities targeted at specific parts of the patient's knee, limb, and muscles.

While the prior art orthotic devices may provide benefits over conventional braces, they still suffer from several disadvantages. One of such disadvantages is that the orthotic devices do not provide multiple forms of pain management with a comprehensive therapeutic treatment of limb, joint or spine disorders involving the bones, cartilage, tendons, ligaments, muscles, nerves, and/or discs that suffer from arthritis or other damage. Another such disadvantage of the prior art is that they do not incorporate biofeedback monitoring and data to improve response to treatment. The prior art orthotic devices provide selective therapy and pain relief limited to a few bodily parts, such as only the muscles and joint. Consequently, such treatment allows for restoration of certain bodily parts while allowing continued deterioration of other bodily parts.

SUMMARY OF THE INVENTION

An object of the present invention is to remedy the problem of selective treatment and pain relief, without the use of feedback information, of orthotic devices. The present invention accommodates a patient with a brace, sleeve, soft pliable pad, or any combination of the three that can be adapted to any area of the body for unloading support, rehabilitation, and therapeutic treatment, and a plurality of electrodes for transmitting a combination of different electrophysical modalities for improved rehabilitation and pain management of joint, limb or spine disorders involving the bones, cartilage, tendons, ligaments, muscles, nerves, or discs. The plurality of electrophysical modalities include neuromodulating functional electrical stimulation (FES) for muscle contractions, transcutaneous electrical nerve stimulation (TENS) for pain management, pulsed electromagnetic field (PEMF) stimulation for cartilage/tissue rejuvenation and pain control, and heat therapy for pain relief. Noted herein, the term "electrodes" encompasses any conductive materials and devices, including electrical coils, electrical plates, electrical conductors, and conductive fabrics and gels.

It is another object of the present invention to provide an orthotic device that can transmit a plurality of electrophysical modalities in a controlled sequence or in a simultaneous manner to the patient's joint, limb, spine, other bodily area. With controlled application of different forms of stimulation, an improved therapy of bodily parts suffering from musculoskeletal conditions is accomplished.

It is an additional object to provide an orthotic device that can apply a plurality of electrophysical modalities to targeted areas of the body, thus enhancing rehabilitative treatment of certain joint, limb, and spine disorders involving the bones, cartilage, tendons, ligaments, muscles, nerves, and/or discs.

These and other objectives are achieved by providing an orthotic device utilizing a brace, sleeve, or flexible pad—alone or in combination—to which electrodes are attached and distributed along an inner surface of the brace, sleeve, or flexible pad and a stimulation control unit, wherein the control unit directs the electrodes to transmit a plurality of electrophysical modalities to a patient's limb. As a result of the sleeve or flexible pad being attached to either the brace or directly to the patient's skin, or a combination of both attachment methods, the brace, sleeve, and/or flexible pad provides medial and lateral unloading support against weight-bearing forces exerted on the limb or provides stabilizing forces or range of motion to the area involved.

These and other objectives are also achieved by providing a non-invasive device for treating bodily parts suffering from deterioration caused by a musculoskeletal disorder, wherein said device includes a brace, sleeve, or flexible pad for unloading support, a plurality of electrodes disposed on the brace, sleeve, or flexible pad, and a stimulation control unit controlling the electrodes for transmission of at least three electrophysical modalities chosen from a group consisting of neuromodulating FES, TENS, PEMF stimulation, and heat therapy stimulation. The stimulation control unit also provides for a user to program a controlled sequence of transmission of the at least three electrophysical modalities. In some embodiments, the controlled sequence is defined by each of the electrodes transmitting one of the at least three electrophysical modalities simultaneously. In other embodiments, the controlled sequence is defined by all of the electrodes simultaneously transmitting the same one of the at least three electrophysical modalities. In yet other embodiments, the controlled sequence is defined by a series transmission of the at least three electrophysical modalities by all of the electrodes. In further embodiments, the controlled sequence is defined by select groups of electrodes transmitting simultaneously or sequentially one of the at least three electrophysical modalities. The above embodiments are not exhaustive of all controlled sequences with which the stimulation control unit can be programmed.

Other objectives of the invention are achieved by providing a non-invasive device for treating musculoskeletal bodily parts suffering from deterioration caused by a musculoskeletal disorder, wherein said device includes a brace for unloading support, a sleeve or flexible pad, a plurality of electrodes disposed on the sleeve or flexible pad, and a stimulation control unit controlling the electrodes for transmission of at least three electrophysical modalities chosen from a group consisting of FES, TENS, PEMF stimulation, and heat therapy stimulation. The sleeve or flexible pad also includes fasteners for removably attaching the sleeve or flexible pad to an inner surface of the brace and thus allowing for the brace to be easily removed from or attached to the sleeve or flexible pad.

Further objectives are achieved by providing a non-invasive device for treating a musculoskeletal disorder, including a brace, sleeve, or flexible pad for unloading support, a plurality of electrodes disposed on the brace, sleeve, or flexible pad, a stimulation control unit controlling the electrodes for transmission of at least three electrophysical modalities chosen from a group consisting of FES, TENS, PEMF stimulation, and heat therapy stimulation, and a plurality of conductors operably connecting the electrodes to the stimulation control unit. The conductors provide for two-way communication between the electrodes and the stimulation control unit. In particular, the stimulation control unit communicates a controlled sequence of transmission of the at least three electrophysical modalities to each of the electrodes while the electrodes supply anatomical data to the control unit.

Additional objectives are achieved by providing a non-invasive device for treating a musculoskeletal disorder, including a brace, sleeve, or flexible pad, a plurality of electrodes disposed on the brace, sleeve, or flexible pad, a stimulation control unit controlling the electrodes for transmission of at least three electrophysical modalities chosen from a group consisting of FES, TENS, PEMF stimulation, and heat therapy stimulation, and a plurality of transmitter-receiver units individually disposed within each of the electrodes and the stimulation control unit. The transmitter-receiver units provide two-way wireless communication, which allows the stimulation control unit to manage specific electrodes according to a controlled sequence of transmission of the electrophysical modalities. The electrodes provide feedback data to the control unit for in-depth analysis of anatomical responses.

Other objectives of the invention are achieved by providing a non-invasive device for treating a musculoskeletal disorder having a brace, sleeve, or flexible pad, a plurality of electrodes disposed on the brace, sleeve or flexible pad, each electrode transmitting a plurality of electrophysical modalities, and a stimulation control unit having a neuromuscular feedback component and a neurofeedback mechanism to dynamically control the transmission of a FES modality and a TENS modality, respectively. The neurofeedback mechanism further comprises pain assessment and pain measurement algorithms, which provide subjective and objective analyses of pain and correlations thereof. When integrated with the feedback control loops of the control unit, these algorithms assess anatomical and neurological responses to the TENS modality. The stimulation control unit also includes a biomechanical component for monitoring biomechanical response and analyzing range of motion of a limb and joint. With the electrodes—or other electrically conductive elements—incorporated into the non-invasive device, the biomechanical component, the neuromuscular feedback component, and the neurofeedback mechanism can be utilized alone or in combination to provide feedback to the control unit. This feedback can come in the form of either individual data point readouts, sent at once or in a sequential data point progression, or multiple data point readouts, sent at a single time point or over sequential time points. Using this feedback, the stimulation control unit dynamically controls the transmission of the FES, TENS, PEMF stimulation and heat therapy stimulation modalities.

Also thus provided is a method of transmitting electrophysical modalities to a bodily part with a non-invasive device, including the steps of at least programming a controlled sequence of transmission of at least three electrophysical modalities, wherein the controlled sequence comprises at least a transmission of one of the electrophysical modalities by one or more electrodes, transmitting the electrophysical modality transcutaneously, observing and recording a response of a muscle mass via a neuromuscular feedback component, and adjusting the controlled sequence according to the response by adjusting a magnitude of the electrophysical modality. Another method of transmitting electrophysical modalities includes the above steps as well as adjusting a duration of the transmission of the electrophysical modality. Yet another method of transmitting electrophysical modalities with a non-invasive device includes the steps of at least programming a controlled sequence of transmission of at least three electrophysical modalities, wherein the controlled sequence comprises at least a transmission of a first modality of the electrophysical modalities by one or more electrodes, transmitting the first modality transcutaneously, observing and recording a response of a muscle mass via a neuromuscular feedback component, and adjusting the controlled sequence by changing the first modality to a second modality.

Yet another method of controlling and assessing the response of transmission of electrophysical modalities to a bodily part include using a neurofeedback mechanism. The neurofeedback mechanism monitors and records activity in at least one nerve and adjusts the controlled sequence according to the activity either by tuning the magnitude and/or duration of a first modality or changing the first modality to a second modality. As examples, the neurofeedback mechanism may be implemented into the non-invasive device by incorporating any one or combination of a Nerve Conduction Test, Electromyogram, or Somatosensory Evoked Potential. Such configurations establish feedback loops to analyze and assess nerve function, which is useful for instance when nerve irritation or nerve compromise is part of the patient's medical problem. The neurological monitoring of the present invention is especially beneficial to patients recovering from operations involving the nervous system or patients having nonoperative musculoskeletal pathology where improved function resulting from use of the invention might pose risk to or cause otherwise occult changes to the musculoskeletal system's anatomic or physiologic integrity. With the neurofeedback mechanism, the control unit generally carries out two major tasks: (1) selective activation of stimulating electrodes with appropriate timing, and (2) recording, processing and displaying of electrophysiologic signals of the limb detected by the electrodes. A healthcare professional (e.g. neurophysiologist) can thus observe and document in real-time the electrophysiologic signals as they change under the influence of the electrophysical modalities, whether it be TENS, FES, PEMF stimulation, or heat therapy stimulation.

Additional methods of transmitting electrophysical modalities to a bodily part include using a biomechanical component for analyzing biomechanical response—such as computerized gait analysis and range of motion analysis—of the limb and adjusting one or more of the modalities in the controlled sequence of transmission according to the biomechanical response and outcome of the computerized analysis.

Each of the neuromuscular feedback component, neurofeedback mechanism, and biomechanical component can be adjusted through the stimulation control unit via interactive software. The interactive software further provides the capability of interfacing with other medical application programs developed by third-parties.

Information obtained from the various biomechanical, neuromuscular and neuro feedback loops can be utilized in CAD (Computer Aided Design) and CAM (Computer Aided Manufacturing) considerations when performing brace "fittings" or customizing individual braces. This would also apply to braces manufactured and sold "off the shelf" with standard sizes and features. For example, a generic brace or universal brace module can be applied to the patient during a trial or fitting session, and with data from the modalities and biofeedback information collated during the fitting session, one can manufacture and develop a personalized brace tailored specifically for that particular patient's needs, anatomy, and body mechanics. Moreover, a improved generic brace for wide segments of the population with more general needs can be developed and modified based on overall data collected from the above described feedback information.

Further provided is a non-invasive device for treating a joint disorder, including a brace, sleeve, or flexible pad for unloading support or other force or support-related purposes, a sleeve or flexible pad removably attached to an inner surface of the brace, a plurality of electrodes disposed on the sleeve or flexible pad, and a stimulation control unit which controls the electrodes to transmit a plurality of electrophysical modalities comprising FES, TENS, PEMF stimulation, and heat therapy stimulation.

The non-invasive orthotic rehabilitation device according to the present invention improves the treatment and rejuvenation of bodily parts, including muscles, cartilage, ligaments and bones, that have been adversely affected by a joint disease. It increases the efficacy of pain relief by applying different forms of pain management electrophysical modalities to the bodily parts. Furthermore, with the device transmitting at least three electrophysical modalities, the present invention avoids the tendency of rejuvenating one bodily part while allowing other bodily parts, including joints, limbs, bones, cartilage, tendons, ligaments, muscles, nerves, or discs, to deteriorate.

Other features and aspects of the invention will become apparent from the following detailed description, taken in conjunction with the accompanying drawings, which illustrate by way of example, the features in accordance with embodiments of the invention. The summary is not intended to limit the scope of the invention, which is defined solely by the claims attached thereto. The summary presents as an example a knee unloading brace. Similar applications include, but are not limited to: weight-bearing braces, loading braces, unloading braces of any kind, such as for the ankle, knee, or hip, range of motion and stabilization braces for the ankle (e.g. ankle support systems and air casts), knee (e.g. patellar cutout braces), and hip, cervical, thoracic and lumbar spine braces (e.g. TLSO), as well as finger, wrist, elbow, and shoulder braces and related medical devices.

The embodiments as discussed above are illustrative and are not intended to exhaust all possible arrangements, modifications, and variations of features of the invention—such as any other neuro-electrodes/electrical impulse type electrodes or feedback combinations—which are ascertainable by those skilled in the art.

DETAILED DESCRIPTION OF THE INVENTION

As used herein, the terms "lateral," "medial," "anterior," "posterior," "upper," and "lower" characterize certain elements of the orthotic device, and in particular, describe the relative proximity of the given element to the central longitudinal axis of the body (i.e. limb) of the user when the orthotic device is mounted thereon. The term lateral means away from a vertical central longitudinal axis of the body, the term medial means toward a vertical central longitudinal axis of the body, the term anterior means toward the front of the body, the term posterior means toward the back of the body, the term upper means higher up on the body above a joint, and the term lower means lower down on the body below a joint.

As used herein, the terms "electrode" and "electrodes" encompass electrical coils, electrical plates, electrical conductors, conductive fabrics and gels, and any other conductive materials and devices.

Figure 1:
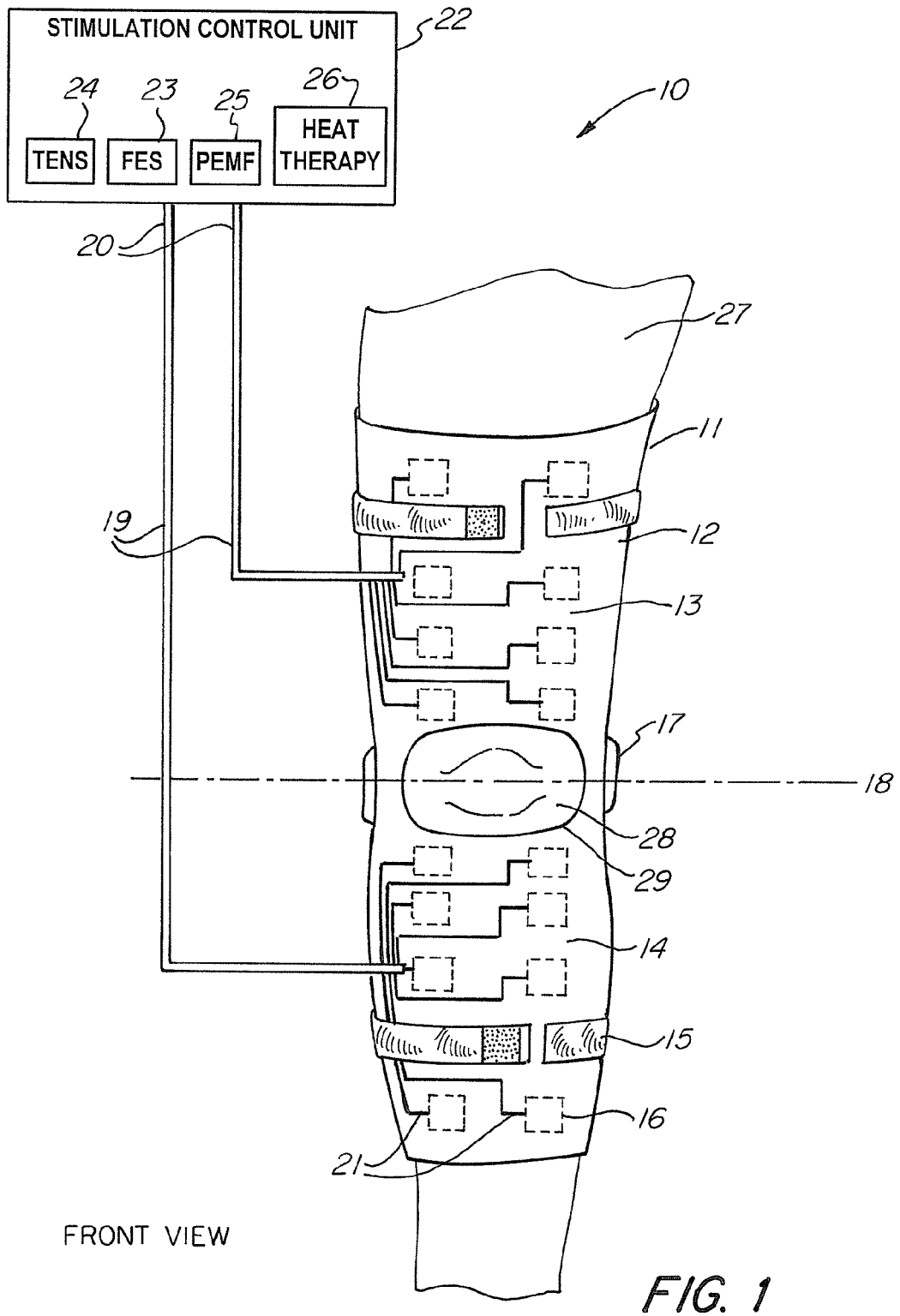
FIG. 1 is a front view of an orthotic device transmitting a plurality of electrophysical modalities according to an exemplary embodiment of the present invention.
Figure 2:
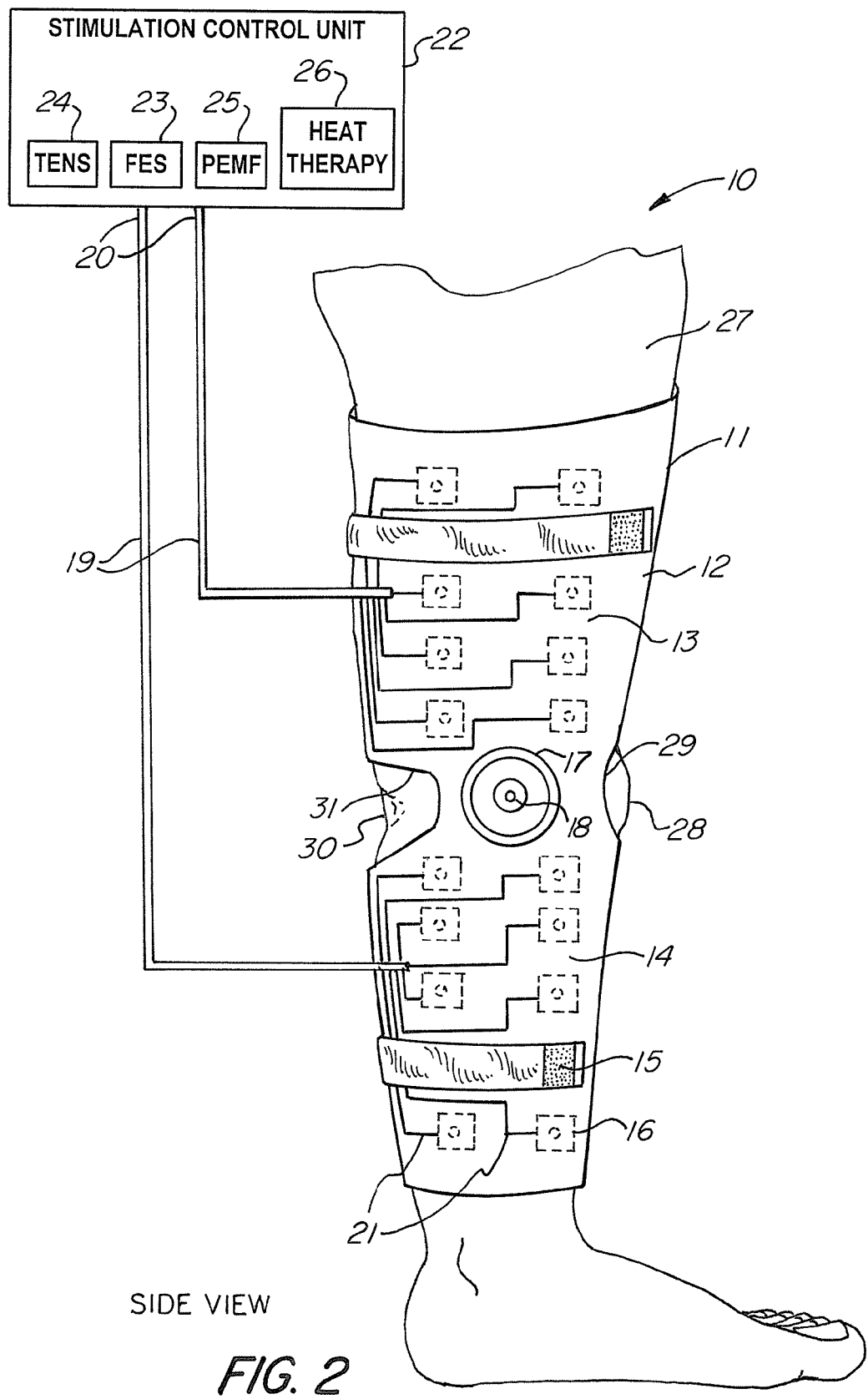
FIG. 2 is a side view of the orthotic device shown in FIG. 1.
Figure 3:
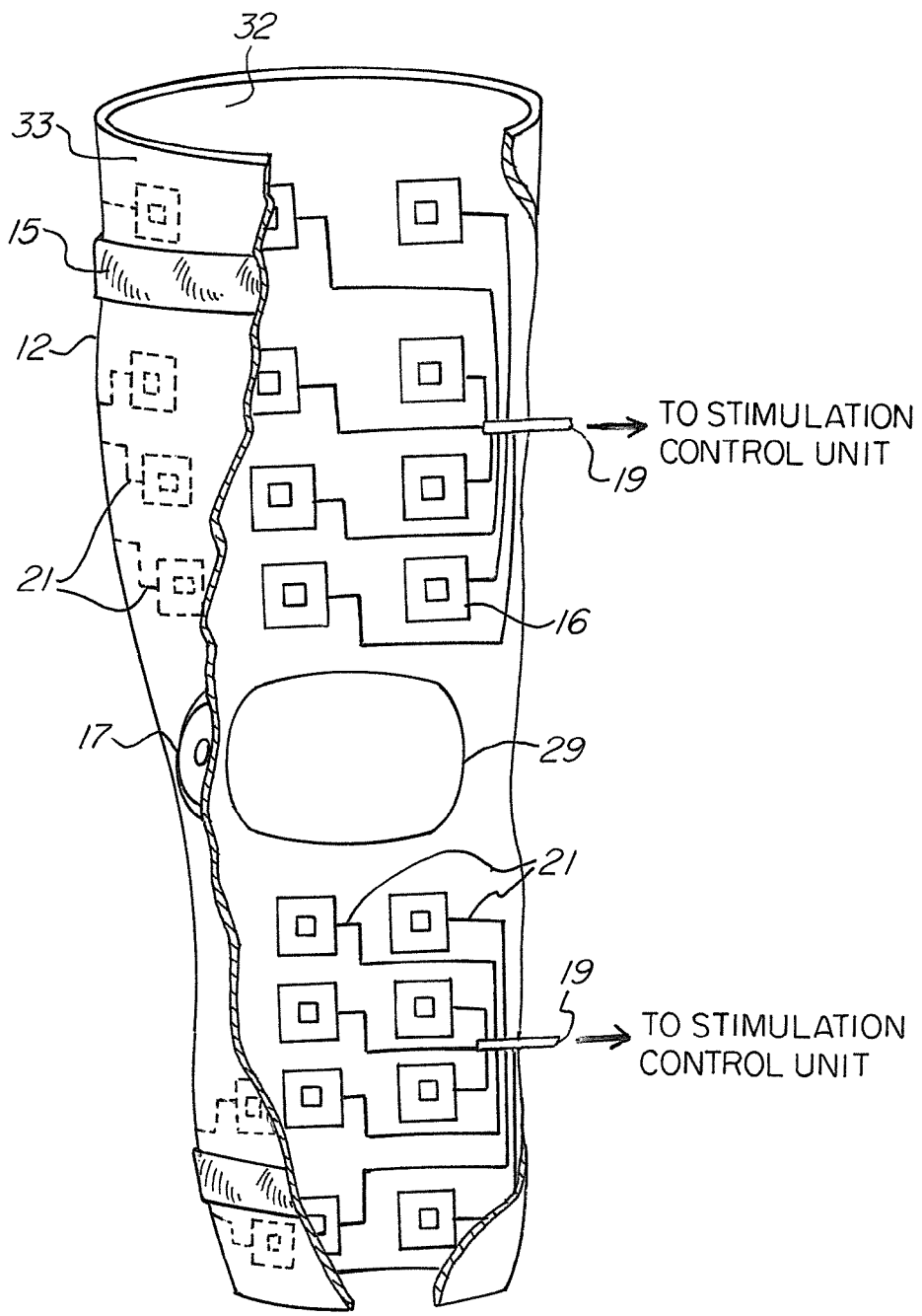
FIG. 3 is a cut-away perspective view of the inside of the orthotic device shown in FIG. 1.

Referring to the figures in detail and first to FIGS. 1-2, there is shown an exemplary embodiment of a non-invasive, orthotic device with electrodes for transmitting electrophysical modalities. FIG. 1 shows the orthotic device 10 with electrodes 16 disposed along the entire length of a brace 11. The orthotic device 10 includes a brace 11 having one support member 12, a plurality of electrodes 16 attached to the brace 11, and a stimulation control unit 22, wherein the stimulation control unit 22 directs the electrodes 16 to transmit electrophysical modalities in a transcutaneous manner to the user's limb, such as the user's leg 27. The support member 12 has an upper portion 13 conforming to the leg 27 above the knee 28 (i.e. thigh) and a lower portion 14 conforming to the user's leg 27 below the knee 28 (i.e. calf). The upper and lower portions 13, 14 each have at least one brace fastener 15 adapted to secure the support member 12 to the leg 27. The brace fasteners 15 can comprise different materials and different configurations that provide a secure, non-slip engagement of the support member 12 to the leg 27. For example, the brace fastener 15 can comprise a VELCRO® strap which is threaded through a retainer (not shown) disposed on the support member 12. Further, the brace fasteners 15 are removably attached to an outer surface 33 (see FIG. 3) of the support member 12, such that the brace fasteners 15 can be repositioned along the upper portion 13 and lower portion 14 to achieve a secure engagement.

When a secure engagement between the support member 12 and the leg 27 is created, the support member 12 provides medial and lateral unloading support for weight-bearing forces exerted on the leg 27 and the knee 28. The support member 12 can also provide comfort to the knee 28. In another embodiment, the support member 12 provides stabilizing forces to the leg 27 and the knee 28. In yet another embodiment, the support member 12 provides range of motion to the leg 27.

The brace 11 further comprises a pair of brace hinges 17 mounted on the brace 11 at opposing sides of the knee 28 where the upper portion 13 meets the lower portion 14. The brace hinges 17 provide for a pivoting motion between the upper portion 13 and the lower portion 14 along an axis 18. The brace hinges 17 thus allow for articulation of the leg 27 or can maintain the leg 27 in one or more selected positions while constantly providing medial and lateral unloading support. As shown in FIG. 2, the brace 11 also includes an anterior patella opening 29 extending the perimeter of the knee 28 and a posterior knee pit opening 31 extending the perimeter of the knee pit 30 when the orthotic device 10 is worn by the user. The patella opening 29 and the knee pit opening 31 provide the necessary openings to avoid any interference the brace 11 may have with the knee 28 and knee pit 30, respectively, when the leg 27 articulates.

The plurality of electrodes 16 disposed along the length of the support member 12 are removably attached to an inner surface 32 (see FIG. 3) of the support member 12. As such, the electrodes 16 do not interfere with the function of the brace fasteners 15, which are disposed on the outer surface 33. The electrodes 16 can be positioned anywhere and in any configuration (e.g. parallel, series, staggered, etc.) on the inner surface 32, including the anterior and posterior of both the upper portion 13 and the lower portion 14. As shown in FIG. 1, the electrodes 16 are disposed on the posterior of both the upper and lower portions 13, 14 in a substantially series-parallel configuration. In FIG. 2, the electrodes 16 are disposed on a side of the support member 12 at the posterior and anterior of both upper and lower portions 13, 14. However, to maximize the treatment benefits of the electrophysical modalities, the electrodes 16 can be positioned closely around specific parts of the leg 27 that require concentrated therapy and pain relief compared to other parts of the leg 27.

The orthotic device 10 also includes conductors 19 each having a proximal end 20 operably connected to the stimulation control unit 22 and a distal end 21 operably connected to at least one of the electrodes 16. The conductors 19 provide for communication between the stimulation control unit 22 and the electrodes 16 in order to control the transmission of the electrophysical modalities. In one embodiment, the stimulation control unit 22 directs the electrodes 16 to transmit electrophysical modalities, wherein the electrophysical modalities comprise at least three electrophysical modalities chosen from a group consisting of neuromodulating FES 23, TENS 24, PEMF stimulation 25, and heat therapy stimulation 26. In another embodiment, the stimulation control unit 22 directs the electrodes 16 to transmit electrophysical modalities comprising FES 23, TENS 24, PEMF stimulation 25, and heat therapy stimulation 26.

The stimulation control unit 22 further establishes a controlled sequence of transmission of the electrophysical modalities. In one embodiment, the controlled sequence of transmission is defined by a first group of electrodes transmitting a first modality of the electrophysical modalities, a second group of electrodes transmitting a second modality of the electrophysical modalities, and a third group of electrodes transmitting a third modality of the electrophysical modalities, wherein the first, second, and third groups simultaneously transmit the first, second and third modalities, respectively. In a second embodiment, the controlled sequence of transmission is defined by the electrodes simultaneously transmitting the same electrophysical modalities. In a third embodiment, the controlled sequence of transmission is defined by the electrodes transmitting in series one of the electrophysical modalities. In yet another embodiment, the controlled sequence of transmission is defined by the serial transmission of each of the electrophysical modalities by all electrodes. Note, the above examples are representative but not exhaustive of the controlled sequence of transmission of electrophysical modalities performed by the orthotic device embodying the present invention.

Figure 4A:
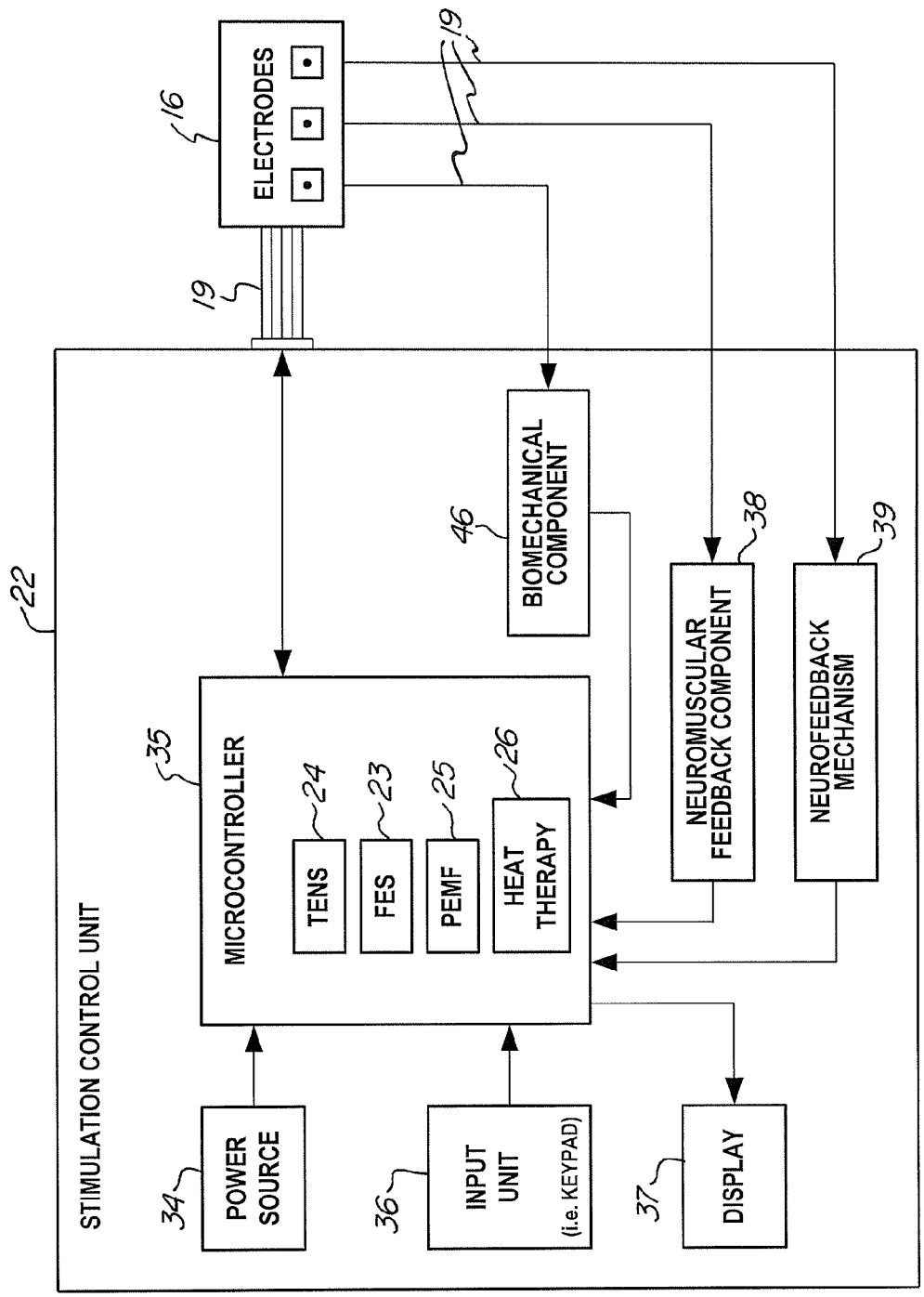
FIGS. 4A and 4B are block diagrams illustrating a stimulation control unit in communication with electrodes for controlling the transmission of a plurality of electrophysical modalities according to an exemplary embodiment of the present invention.

FIG. 4A shows a block diagram of one embodiment of the stimulation control unit. The stimulation control unit 22 comprises a power source 34 for supplying energy to the control unit 22, a microcontroller 35 for controlling the electrodes 16 according to the controlled sequence of transmission of the at least three electrophysical modalities chosen from the group consisting FES 23, TENS 24, PEMF stimulation 25, and heat therapy stimulation 26, an input unit 36 for manipulating and programming the controlled sequence of transmission into the microcontroller 35, and a monitor 37 for displaying the controlled sequence of transmission and a status of each of the electrodes 16. In one embodiment, the power source 34 comprises an energy cell or portable battery pack. In another embodiment, energy is supplied to the stimulation control unit 22 through an electrical cord (not shown) having one end connected to the control unit 22 and another end connected to an electrical socket. With regards to the input unit 36, one embodiment of this element comprises an alpha-numeric keypad or keyboard. In an alternative embodiment, the input unit 36 is combined with the monitor 37 to provide a touch screen interface responsive to a touch by the user.

With the input unit 36 and the monitor 37 coupled to the microcontroller 35, the user can create one or more controlled sequences of transmission of the electrophysical modalities, save the controlled sequences, and select at a later time any one of the saved controlled sequences. Once the user makes a selection, the microcontroller 35 communicates the controlled sequence to each of the electrodes 16 via the conductors 19. In one embodiment, the stimulation control unit 22 also includes a neuromuscular feedback component 38 connected to the microcontroller 35 and electrodes 16 via conductors 19. With the electrodes 16, the neuromuscular feedback component 38 observes and records a response in a muscle mass upon the transmission of a FES modality 23. The neuromuscular feedback component 38 then adjusts the FES modality 23 according to the response and controlled sequence of transmission. Specifically, the neuromuscular feedback component 38 can change a parameter (e.g. magnitude or duration) of the FES modality 23. The neuromuscular feedback component 38 may also modify the controlled sequence of transmission by adjusting the electrophysical modality from FES 23 to TENS 24, PEMF stimulation 25, or heat therapy stimulation 26. In another embodiment, the stimulation control unit 22 includes a neurofeedback mechanism 39 connected to the microcontroller 35 and the electrodes 16 via conductors 19. Similar to the configuration of the neuromuscular feedback component 38, the neurofeedback mechanism 39 observes and records a response in a nerve or group of nerves upon the transmission of a TENS modality 24. The neurofeedback mechanism 39 then adjusts the TENS modality 24 according to the response. For example, the neurofeedback component 38 can change the magnitude or duration of the TENS modality 24 or modify the controlled sequence of transmission by adjusting the electrophysical modality from TENS 24 to FES 23, PEMF stimulation 25, or heat therapy stimulation 26. The neurofeedback mechanism 39 can be based on incorporating a Nerve Conduction Test, Electromyograph, Somatosensory Evoked Potential (SSEP), or other neuro-electrode/electrical impulse type electrode. In yet another embodiment, the stimulation control unit 22 includes both the neuromuscular feedback component 38 and the neurofeedback mechanism 39 to adjust the controlled sequence of transmission.

According to another embodiment of the present invention, the stimulation control unit 22 has a biomechanical component 46 connected to the electrodes 16 via conductors 19. As an alternative, a separate set of conductors can be used to operably connect the biomechanical component 46 to the electrodes 16. Regardless of whether conductors 19 or a separate set of conductors are used, the biomechanical component 46 monitors biomechanical response in the limb and performs computerized gait analysis and range of motion analysis throughout the operation of the orthotic device 10. Based on the biomechanical response and analysis viewed within the context of the controlled sequence of transmission, the biomechanical component 46 can adjust the FES modality 23 and/or the TENS modality 24. Moreover, the biomechanical component 46 can adjust the PEMF stimulation 25 and/or the heat therapy stimulation 26 according to the biomechanical response. With regards to the PEMF stimulation 25, the biomechanical component 46 can vary several aspects of the electromagnetic field, including the frequency, intensity, the type of waveform (e.g. sine, square, triangle, sawtooth, or random), and therapy time. The biomechanical component 46 will adjust the PEMF stimulation 25 to maximize its therapeutic benefit on the user's leg 27 and knee 28. Similarly, the biomechanical component 46 can adjust the heat therapy stimulation 26 by either increasing or decreasing the temperature applied to the user's body to promote healing in the limb, joint, muscles, and other bodily parts. In particular, pain relief and vasodilation for muscle relaxation can be accomplished by transmitting warm-to-hot temperatures to the limb and joint while transmitting cool-to-cold temperatures reduces inflammation and decreases pain and spasms. By incorporating, either alone or in combination, the neuromuscular feedback component 38, neurofeedback mechanism 39, and the biomechanical component 46 with the microcontroller 35, a dynamic feedback control of the transmission of electrophysical modalities can be achieved. The feedback from each of the electrodes 16 can be unique, individual data point readouts, sent to any of the three feedback components either all at once or in a sequential data point progression. Alternatively, the feedback from each of the electrodes 16 can be multiple data point readouts acquired at single time point or over sequential time points.

The data obtained from the biomechanical, neuromuscular, and neuro feedback loops is not only beneficial in providing a real-time, intelligent form of control but can be used in CAD (Computer Aided Design) and CAM (Computer Aided Manufacturing) considerations for brace "fitting" or customization of braces. For example, data from the modalities and biofeedback information can be collated during a brace fitting session to manufacture and develop a customized brace tailored for a particular individual's needs, anatomy, and body mechanics. In another example, an improved generic brace for wide segments of the population with general needs (as opposed to unique medical conditions) can be developed and modified based on overall data collected from the described feedback information.

Figure 4B:
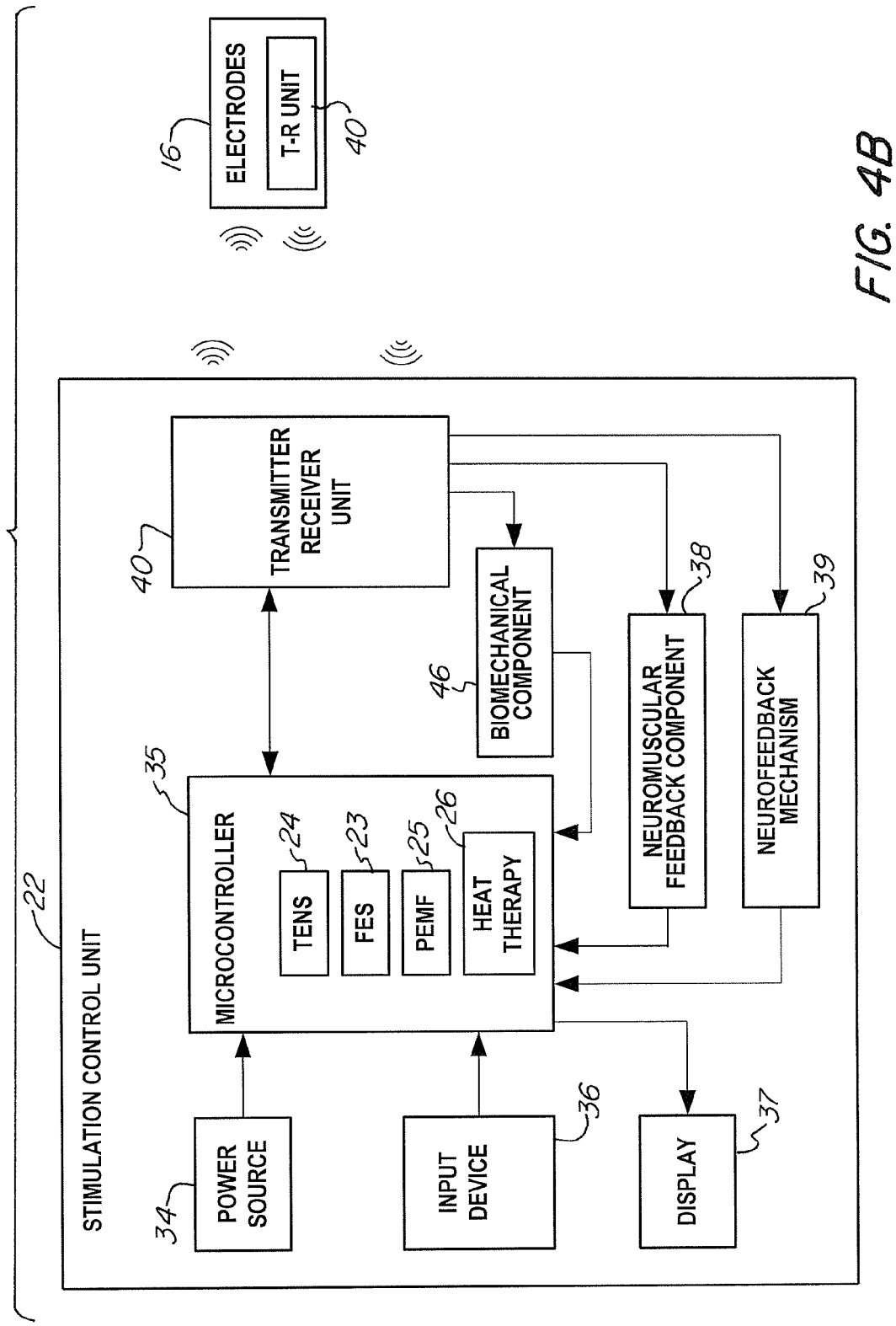

FIG. 4B shows a block diagram of a second embodiment of the stimulation control unit according to the present invention. In this embodiment, the stimulation control unit 22 comprises a power source 34, a microcontroller 35, an input unit 36, a monitor 37, and a transmitter-receiver unit 40. Further, each of the electrodes 16 comprises a transmitter-receiver unit 40. The transmitter-receiver units 40 establish wireless communication between the stimulation control unit 22 and the electrodes 16, thus providing control of the electrodes 16. The transmitter-receiver units 40 also communicate muscle responses and nerve activity from the electrodes 16 to the neuromuscular feedback component 38 and neurofeedback mechanism 39, respectively. Biomechanical response and range of motion data is also sent back wirelessly from the electrodes 16 to the biomechanical component 46.

Figure 5A:
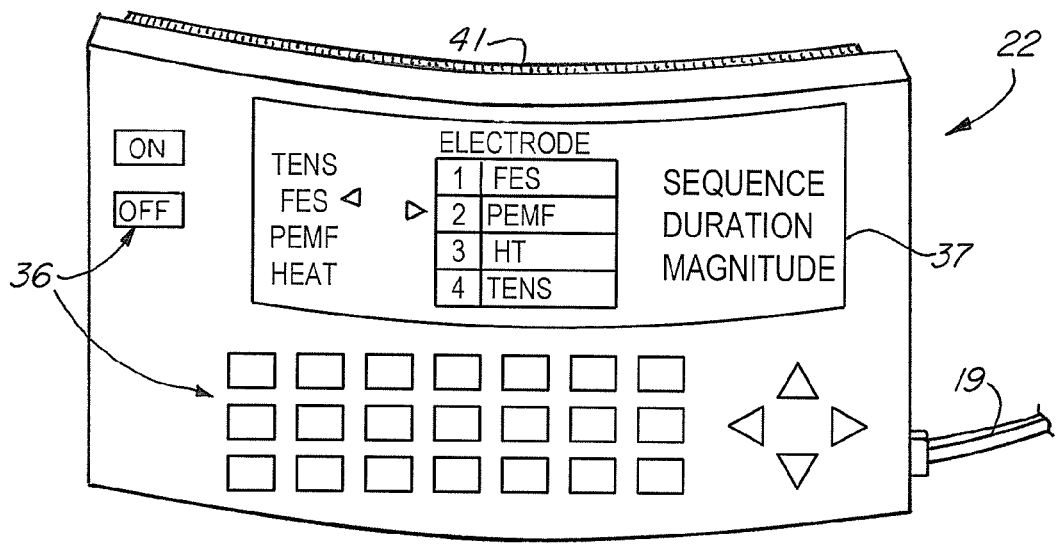
FIG. 5A is a front view of a stimulation control unit for controlling the transmission of a plurality of electrophysical modalities according to an exemplary embodiment of the present invention.
Figure 5B:
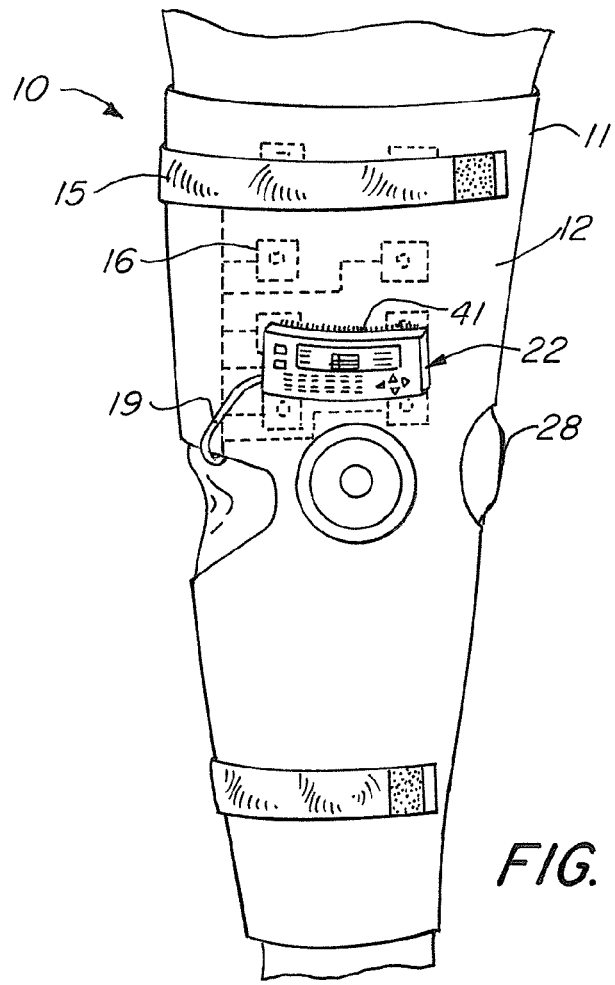
FIG. 5B is a front view of the stimulation control unit of FIG. 5A removably attached to the brace of FIG. 1.

FIG. 5A is a front view of the stimulation control unit 22 as embodied in FIG. 4A. Using the input unit 36, the user can program a controlled sequence of transmission into control unit 22 while viewing a system interface displayed on monitor 37. As shown in FIG. 5B, the stimulation control unit 22 also includes a unit fastener 41 adapted to removably attach the control unit 22 to the outer surface 33 of the support member 12. In one embodiment, the unit fastener 41 can comprise VELCRO® hook-and-loop fastening means. In another embodiment, the unit fastener 41 can comprise a clip which attaches to one of the brace fasteners 15.

Figure 6A:
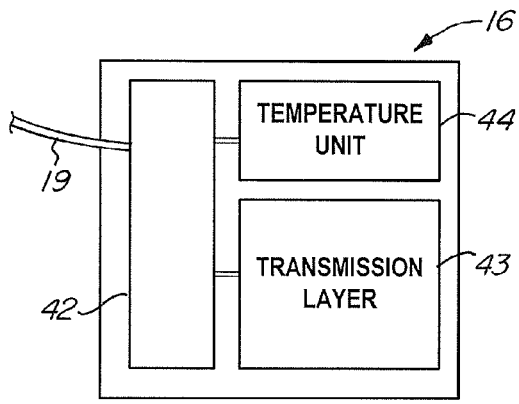
FIGS. 6A and 6B are top views of an electrode in wired communication and wireless communication with a stimulation control unit, respectively.
Figure 6B:
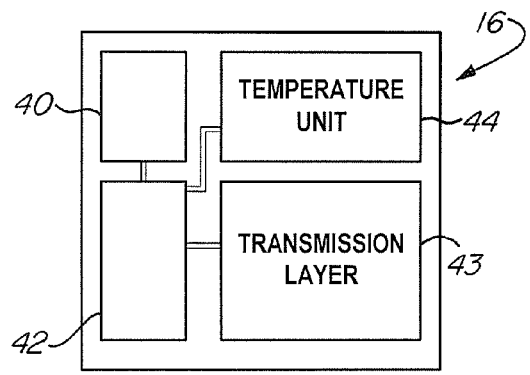

FIGS. 6A and 6B are top views of two embodiments of the electrode 16. In FIG. 6A, the electrode 16 comprises a signal generator 42 connected to conductor 19, a temperature unit 44 and a transmission layer 43, which come in direct contact with the user's leg 27. Signal generator 42 receives and interprets the controlled sequence of transmission from the stimulation control unit 22 and supplies an electrical current to either temperature unit 44 or transmission layer 43 for generating one of the electrophysical modalities. If the electrode 16 is directed to transmit either FES 23, TENS 24, or PEMF stimulation 25, the signal generator 42 supplies the electrical current to the transmission layer 43 which in turn transmits the stimulation to the leg 27. Further, the transmission layer 43 is adapted to monitor a response or activity of a bodily part (e.g. muscle or nerve) and communicate the response back to the microcontroller 35, neuromuscular feedback component 38, neurofeedback mechanism 39, and biomechanical component 46. If the electrode 16 is directed to transmit heat therapy stimulation 26, the signal generator 42 supplies electrical current to the temperature unit 44. The temperature unit 44, which further comprises electrical coils or other similar mechanisms for producing different temperatures, interprets and uses the electrical current to provide either heating or cooling to the user's leg 27. In all embodiments, the electrodes are designed to detect and send electrical impulses and may require special features, such as a conductive gel, to provide for appropriate conductive characteristics.

As illustrated in FIG. 6B, another embodiment of electrode 16 comprises a signal generator 42 connected to a transmitter-receiver unit 40, a temperature unit 44 and transmission layer 43. With the transmitter-receiver unit 40, commands from the stimulation control unit 22 are received wirelessly by the electrodes 16 while responses in bodily parts that are observed by the electrodes 16 are sent back to the microcontroller 35, neuromuscular feedback component 38, neurofeedback mechanism 39, and biomechanical component 46.

Figure 7:
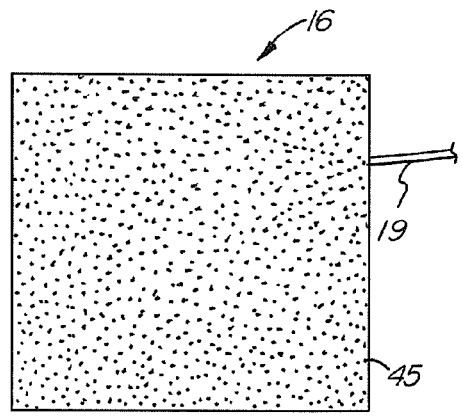
FIG. 7 is a bottom view of the electrode shown in FIG. 6A.

FIG. 7 shows a bottom view of electrode 16. To removably attach the electrode 16 to support member 12, electrode 16 comprises a fastening layer 45 disposed on a side opposite the signal generator 42, transmission layer 43, and temperature unit 44. The fastening layer 45 is adapted to removably attach the electrode 16 to the inner surface 32 of support member 12. In one example, the fastening layer 45 can be made of VELCRO® or some other material that provides adhesion or engagement between the electrode and brace to achieve a secure attachment. Discussed in further detail below, the fastening layer is also adapted to removably attach an electrode to an inner surface of a sleeve or flexible pad, either alone or in combination with a brace.

Figure 8:
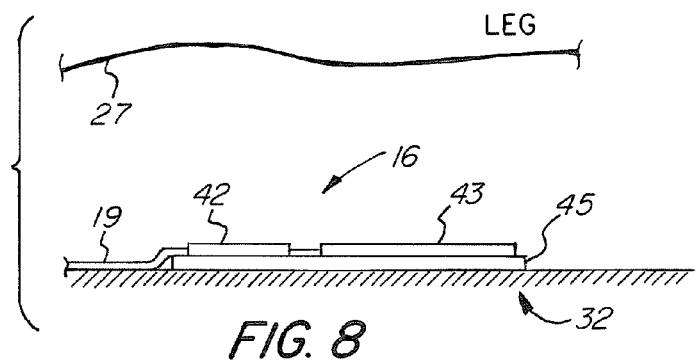
FIG. 8 is a side elevation view of the electrode shown in FIG. 6A.

As illustrated in FIG. 8, the fastening layer 45 is in contact with the inner surface 32 to securely attach the electrode 16 to the support member 12. Once the user positions the orthotic device 10 on his or her leg 27, the electrode 16 is placed in direct contact with the leg 27, allowing for transmission of the electrophysical modalities to be accomplished transcutaneously. Further, the electrode 16 with signal generator 42, temperature unit 44 (not shown), transmission layer 43, and fastening layer 45 still maintains a small footprint. As such, the electrode 16 lies substantially flush with the inner surface 32 of support member 12.

Figure 9:
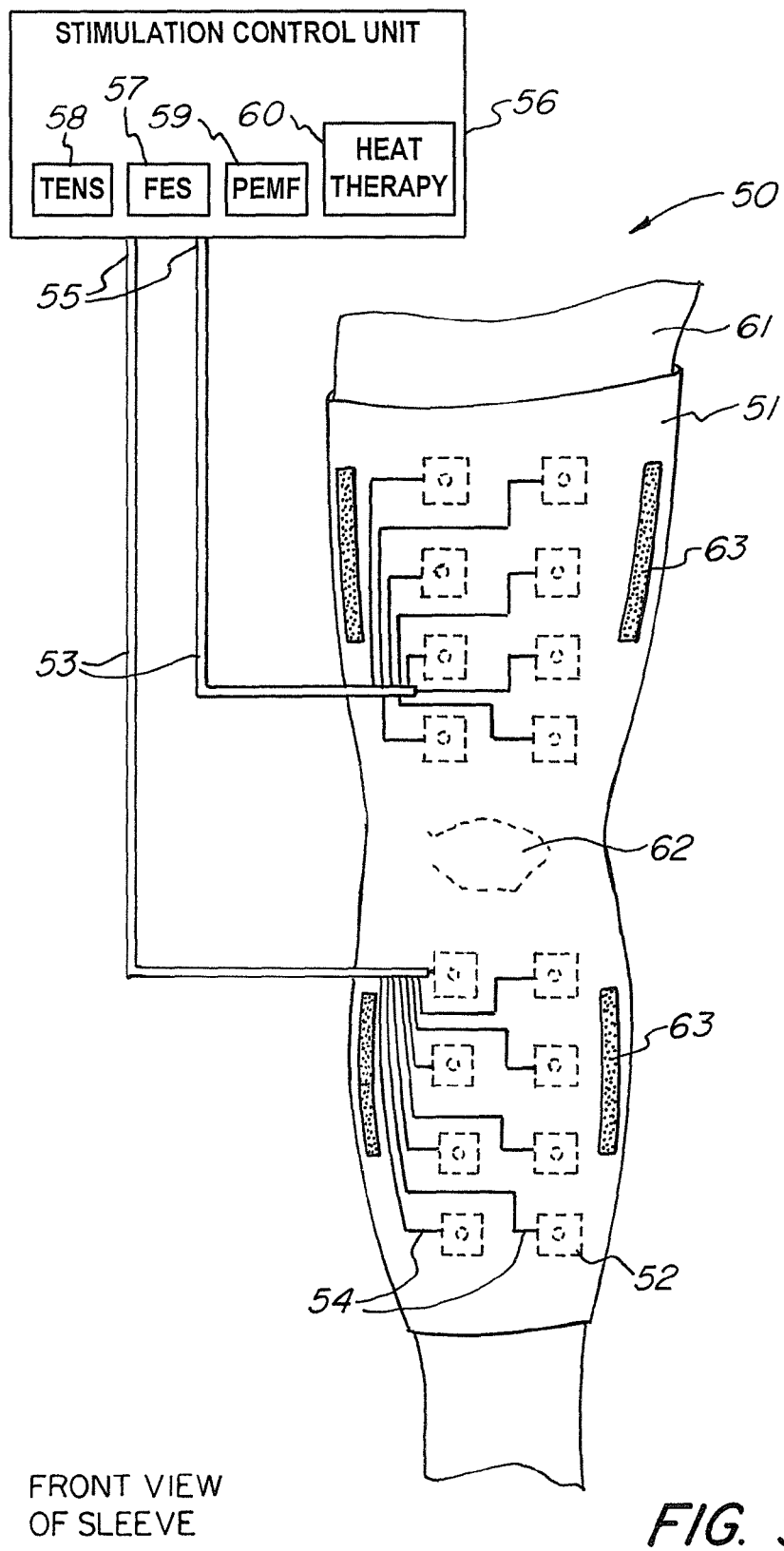
FIG. 9 is a front view of an orthotic device transmitting a plurality of electrophysical modalities according to a second embodiment of the present invention.

Referring to FIG. 9, there is shown a second embodiment of the non-invasive, orthotic device according to the present invention. FIG. 9, in particular, shows an orthotic device 50 having a sleeve 51, electrodes 52 disposed on the sleeve 51, a stimulation control unit 56, and a plurality of conductors 53 each having a proximal end 55 connected to the stimulation control unit 56 and a distal end 54 connected to one or more electrodes 52. The sleeve 51 is made of a material having elastic properties and has a tubular shape designed to fit over and conform to the user's leg 61 and knee 62. More specifically, the sleeve is capable of conforming to any configuration that accommodates the anatomical aspects of the bodily area in question. Further, the sleeve 51 maintains constant contact with the leg 61 and knee 62 while allowing flexibility for motion of the leg 61 and knee 62. Like electrodes 16 (see FIGS. 6A, 6B, and 7), each electrode 52 has a fastening layer for removably attaching the electrode 52 to an inner lining of the sleeve 51, a signal generator for supplying an electrical current needed to generate the electrophysical modalities, a transmission layer adapted to transmit FES 57, TENS 58 and PEMF 59, and a temperature unit adapted to provide heat therapy stimulation 60. Once the user wears the sleeve 51, the transmission layer and temperature unit of each electrode 52 is placed in direct contact with the user's leg 61. In cases involving treatment of anatomical body parts other than the user's leg, the sleeve, when worn, is also capable of placing the transmission layer and temperature unit in direct contact with the body part.

In another embodiment, the electrodes 52 can removably attach to an outer lining of the sleeve 51 such that the transmission layers of the electrodes 52 are in contact with the sleeve 51. With the sleeve 51 comprising conductive fabric, the electrodes 52 can transmit transcutaneously the electrophysical modalities through the sleeve 51 to the user's leg 61. Therefore, in this particular embodiment, the electrodes 52 are not (and need not be) in direct contact with the user's leg 61.

Figure 10:
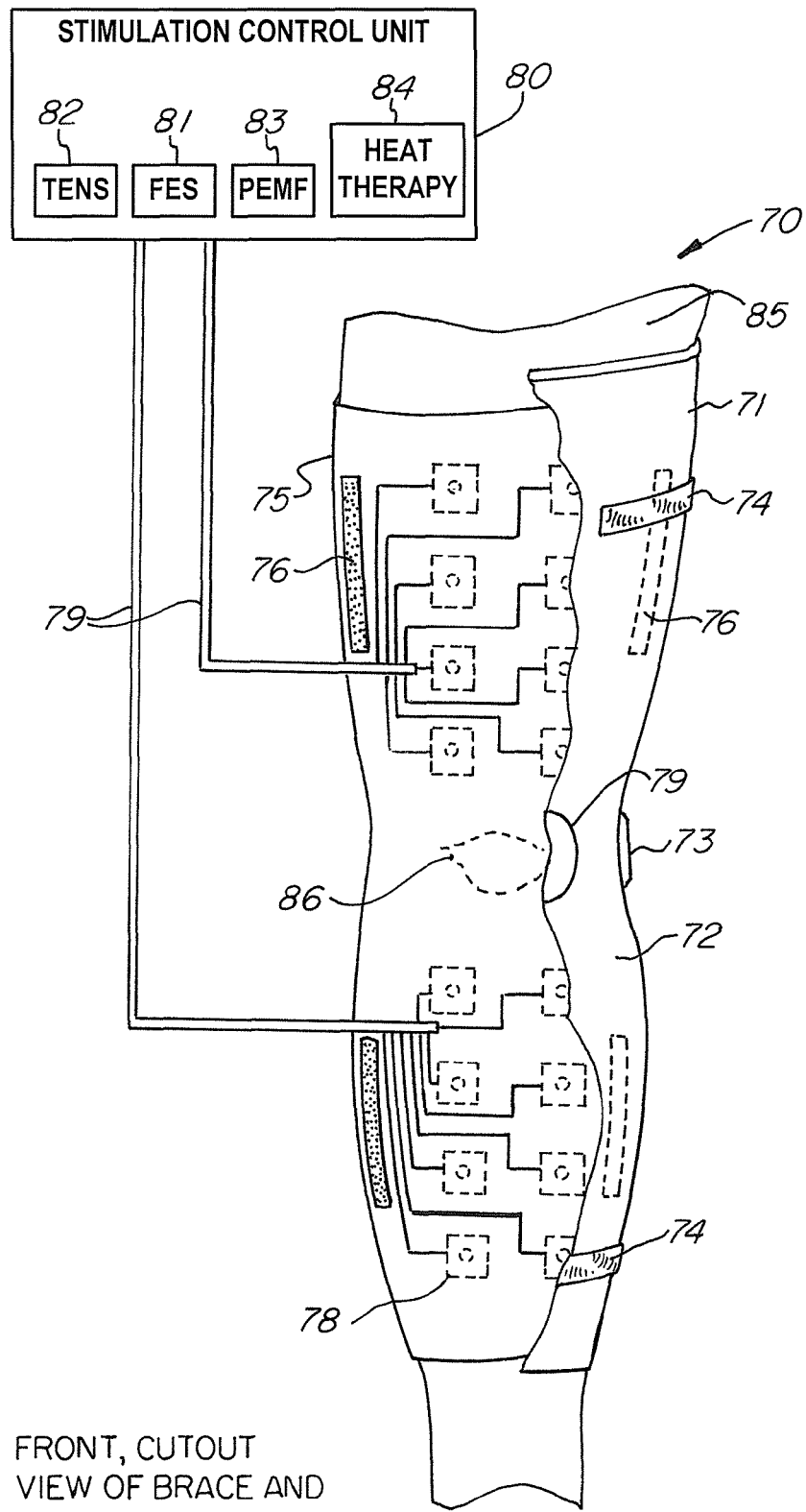
FIG. 10 is a cut-away perspective view of an orthotic device transmitting a plurality of electrophysical modalities according to a third embodiment of the present invention.

Referring to FIG. 10, there is shown a third embodiment of the non-invasive, orthotic device according to the present invention. FIG. 10, in particular, shows an orthotic device 70 having a brace 71, a pair of brace hinges 73 disposed on the brace 71, a sleeve 75, electrodes 78, conductors 79, and a stimulation control unit 80 for establishing a controlled sequence of transmission of electrophysical modalities. The electrodes 78 are removably attached to an inner lining of the sleeve 75 such that the electrodes 78 are in direct contact with the user's leg 85. The sleeve 75 further comprises sleeve fasteners 76 disposed on the outer lining of the sleeve 75 (also shown as 63 in FIG. 9). The sleeve fasteners 76 are adapted to releasably engage the inner surface (not shown) of the brace 71 when the user positions his leg 85 into the brace 71. Once the user is wearing the brace 71, the sleeve fasteners 76 provide a secure attachment between the sleeve 75 and the brace 71 preventing any slipping motion between the two elements. On the other hand, if the user needs to take off the brace 71, the user merely releases the sleeve fasteners 76 from the inner surface of the brace 71. The orthotic device 70 further comprises brace fasteners 74 disposed on an outer surface 72 to secure the brace 71 to the leg 85. When a secure engagement is created, the brace 71 provides medial and lateral unloading support for weight-bearing forces exerted on the leg 85 and knee 86.

Through the conductors 79, the stimulation control unit 80 directs the electrodes 78 to transmit at least three electrophysical modalities chosen from the group consisting FES 81, TENS 82, PEMF 83, and heat therapy stimulation 84. The stimulation control unit 80 is further adapted to removably attach to the outer surface 72 of the brace 71. Alternatively, the stimulation control unit 80 can be a separate stand-alone unit in wireless communication with the electrodes 78.

Figure 11:
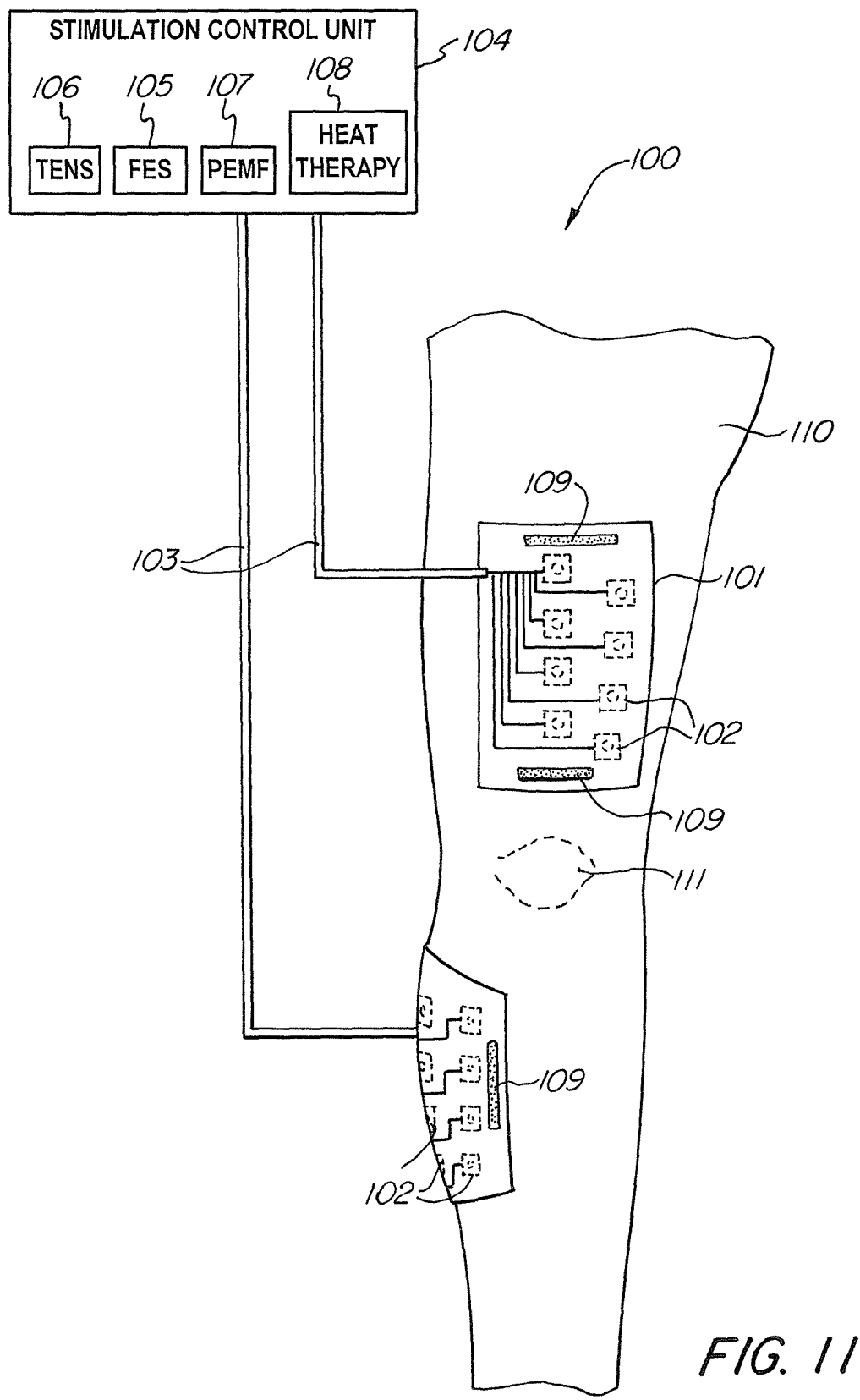
FIG. 11 is a front view of an orthotic device transmitting a plurality of electrophysical modalities according to a fourth embodiment of the present invention.

Referring to FIG. 11, a fourth embodiment of the non-invasive, orthotic device is shown. FIG. 11 illustrates an orthotic device 100 comprising a flexible pad 101, a plurality of electrodes 102 disposed on the flexible pad 101, a stimulation control unit 104, and one or more conductors 103 each having a proximal end connected to the stimulation control unit 104 and a distal end connected to one or more electrodes 102. The flexible pad 101 is made of any material having flexible and elastic characteristics, such as fabric, plastic, or latex rubber, which allows it to conform to any anatomical aspects of the user's leg 110, knee 111, or other body part. In one embodiment, the flexible pad 101 also has an adhesive portion disposed on an inner lining (not shown) of the flexible pad 101 and adapted to removably attach to any part of the user's leg 110. As one example, the adhesive portion comprises a pressure-sensitive adhesive composition. In another example, the adhesive portion can be composed of medical tape. Other materials which can provide a secure, temporary attachment to any part of a user's body can also be used for the adhesive portion. In a different embodiment, the flexible pad 101 uses other means of fastening (e.g. VELCRO® straps) instead of an adhesive portion to secure the pad to the user's body. Where VELCRO straps® are used, the flexible pad can have configurations that resemble existing medical support pads, such as knee pads, leg pads, or lumbar spine pads.

Each of the electrodes 102 comprises a fastening layer for removably attaching the electrode to the inner lining of the flexible pad 101. The fastening layer can comprise VELCRO® or other material that creates a secure engagement between the electrode 102 and the flexible pad 101. Alternatively, the adhesive portion on the inner lining of the flexible pad 101 can be used to removably attach the electrode 102.

The electrodes 102 each have a signal generator for creating at least three electrophysical modalities chosen from the group consisting of FES 105, TENS 106, PEMF stimulation 107, and heat therapy stimulation 108, a transmission layer adapted to transmit the FES 105, TENS 106, and PEMF stimulation 107, and a temperature unit adapted to provide the heat therapy stimulation 108. When the flexible pad 101 is applied to the user's leg 110, direct contact is made between the user's leg and the transmission layer and temperature unit of the electrodes 102. This direct contact allows for transcutaneous transmission of the electrophysical modalities from the electrodes 102 to the user's leg 110.

Figure 12:
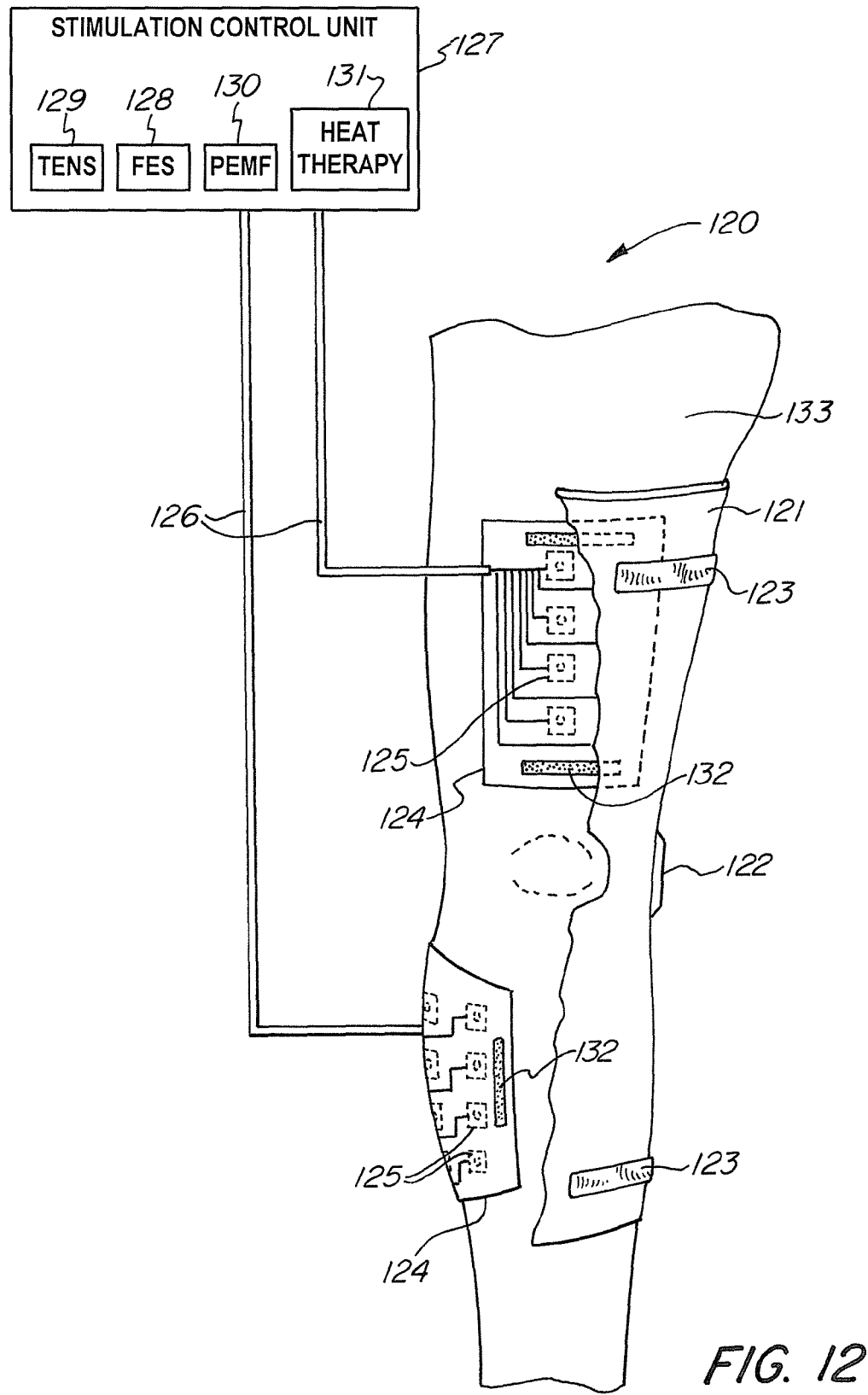
FIG. 12 is a cut-away perspective view of an orthotic device transmitting a plurality of electrophysical modalities according to a fifth embodiment of the present invention.

Referring to FIG. 12, there is shown a fifth embodiment of the non-invasive, orthotic device according to the present invention. FIG. 12 illustrates an orthotic device 120 comprising a brace 121, a pair of brace hinges 122 disposed on opposite sides of the brace 121, one or more brace fasteners 123 for securing the brace 121 to a leg 133, a flexible pad 124, a plurality of electrodes 125, one or more conductors 126, and a stimulation control unit 127 for programming a controlled sequence of transmission of electrophysical modalities (FES 128, TENS 129, PEMF stimulation 120, heat therapy stimulation 131). Having a similar configuration as the third embodiment of the orthotic device shown in FIG. 10, the electrodes 127 are removably attached to an inner lining of the flexible pad 124 so that the electrodes 125 maintain direct contact with the user's leg 133. The pad 124 further comprises pad fasteners 132 (also shown as 109 in FIG. 11) disposed on an outer lining of the pad 124 and adapted to releasably engage the inner surface (not shown) of the brace 121. Once the user applies the flexible pad 124 to his leg 133 and subsequently positions the brace 121 on his leg 133, the pad fasteners 132 create a secure attachment between the flexible pad 124 and the brace 121. If the user needs to take off the brace 121, the user merely releases the pad fasteners 132 to separate the flexible pad 124 from the inner surface of the brace 121.

Further, the pad fasteners 132 promote consistent positioning of the electrodes 125 on the user's leg 133 between different treatment sessions of the orthotic device 120. Specifically, after completing a first treatment session, the user can leave the flexible pad 124 (and electrodes 125) attached to the brace 121 when the brace is removed from the leg 133. When a second treatment session must be conducted, the user simply places the brace 121 on his leg 133 to dispose the electrodes 125 in the same positions (on the leg 133) that they had during the first treatment session. Other means can also be used to promote consistent positioning of electrodes on the limb from one treatment session to another. Anatomical landmarks, skin markers, contours of the sleeve/pad, sleeve/pad cutout locations and fitting parameters, and other positioning characteristics unique to the patient allow for the same electrode positioning features to be incorporated into the sleeve or pad thus maintaining position consistency while donning or removing the sleeve or pad from one treatment session to the next.

This particular feature of the present invention therefore promotes improved therapeutic treatment by ensuring consistent transmission of electrophysical modalities to specific parts of the user's leg from one treatment session to another.

The one or more conductors 126 connect the stimulation control unit 127 to the electrodes 125, which allows the control unit 127 to supply the electrodes 125 with the controlled sequence of transmission of the electrophysical modalities. The stimulation control unit 127 also includes a unit fastener (not shown) for removably attaching the control unit to the flexible pad 124 or the brace 121. In another embodiment, the stimulation control unit 127 can be a stand-alone wireless unit having no physical attachment to either the flexible pad 124 or the brace 121.

Figure 13:
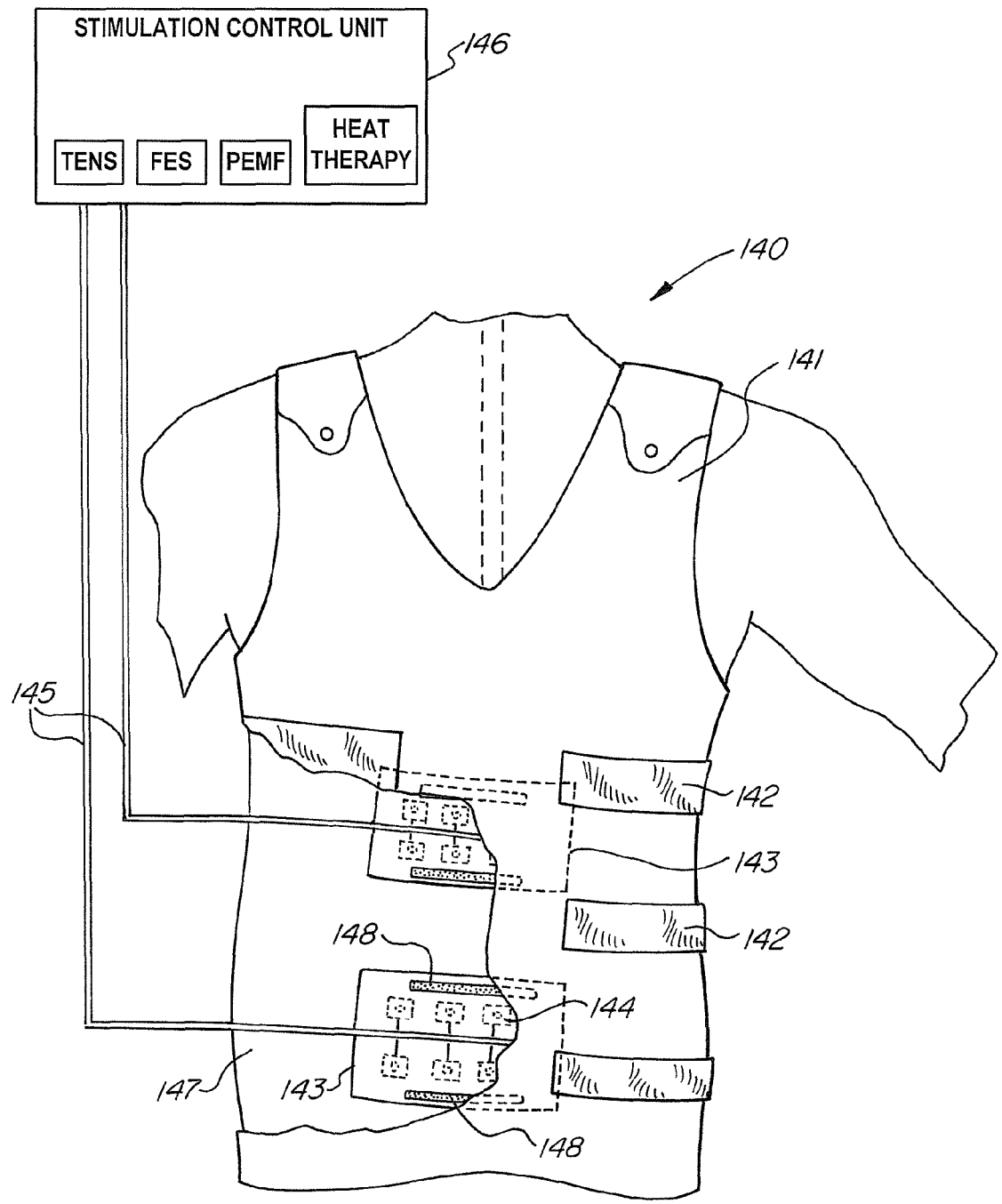
FIG. 13 is a cut-away perspective view of an orthotic device transmitting a plurality of electrophysical modalities according to a sixth embodiment of the present invention.

FIG. 13 shows a sixth embodiment of the non-invasive, orthotic device comprising a back brace. FIG. 13, in particular, shows an orthotic device 140 having a brace 141 positioned around a user's torso 147, a plurality of brace fasteners 142, one or more flexible pads 143, a plurality of electrodes 144, one or more conductors 145, and a stimulation control unit 146. With the electrodes 144 removably attached to an inner lining (not shown) of the flexible pad 143, an adhesive portion disposed on the inner lining provides the means for attaching the flexible pad 143 to the torso 147. Accordingly, direct contact is made between the electrodes 144 and the torso 147. Further, the flexible pads 143 are removably attached to an inner surface of the brace 141 via one or more pad fasteners 148. Once the user is wearing the brace 141, the pad fasteners 148 provide a secure attachment between the flexible pads 143 and the brace 141 and prevent any slipping motion between these two elements.

For all previously discussed embodiments of the present invention, the stimulation control unit also includes the capability of defining user privileges. In particular, the control unit can be configured to provide complete control to a medical practitioner (e.g. doctor, nurse, physical therapist) but only limited control to a patient. The medical practitioner has access to all the features of the control unit, allowing the practitioner to select and/or adjust different parameters for programming a controlled sequence of transmission of a plurality of electrophysical modalities. Further, the medical practitioner can define what privileges the patient can have in operating the orthotic device. In one instance, the patient may only have control over a few of the electrophysical modalities used in the controlled sequence of transmission. For example, the patient may only be able to adjust the heat therapy stimulation modality of a controlled sequence of transmission involving TENS, FES, PEMF, and the heat therapy stimulation modalities. In another instance, the medical practitioner can limit the scope in which the patient can manipulate the transmission of any one of the electrophysical modalities. For example, the patient may have access through the control unit to adjust only the duration and not the magnitude of the FES modality. In view of the above, the stimulation control unit provides a means for user-defined privileges such that patients have restricted access to certain electrophysical modalities and limited control in adjusting certain parameters of the electrophysical modalities. This capability provides a safeguard against a patient inadvertently adjusting the controlled sequence of transmission such that a less-than-optimum form of treatment is provided.

Although the invention has been described with reference to particular arrangement of parts, features, and the like, these are not intended to exhaust all possible arrangements or features, and indeed many modifications and variations will be ascertainable to those of skill in the art. The present invention is designed so that any electrical or mechanical treatment modalities that are available but have not been incorporated into the description of the invention, or that become available as technology advances, are considered part of the invention and incorporated by modifying the electrical and mechanical parts and protocols associated with them to the extent that such additional electrical or mechanical advances encompass any combination of the above described four or more treatment modalities.

What is claimed is:

1. A non-invasive device for assisting treatment of a joint, limb disorder or spine disorder involving the bones, cartilage, tendons, ligaments, muscles, nerves, or discs suffering from a musculoskeletal disorder, the device comprising:
   a brace having at least one support member conforming to a limb and assisting movement in the limb, and at least one brace fastener, wherein the at least one brace fastener is attached to the at least one support member and is adapted to secure the at least one support member to the limb while still allowing for articulation of the limb;
   a plurality of electrodes disposed on the brace, wherein the plurality of electrodes transmit at least the following four electrophysical modalities: neuromodulating functional electrical stimulation (FES), transcutaneous electrical nerve stimulation (TENS), pulsed electromagnetic field (PEMF) stimulation, and heat therapy stimulation;
   wherein said plurality of electrodes comprises a first group transmitting said FES modality, a second group transmitting said TENS modality, a third group transmitting said PEMF modality and a fourth group transmitting said heat therapy stimulation; and
   a stimulation control unit establishing a controlled sequence of transmission of the at least four electrophysical modalities and communicating said controlled sequence to the electrodes.

2. The device of claim 1, wherein the stimulation control unit comprises:
   a power source for supplying energy to the control unit;
   a microcontroller for controlling said plurality of electrodes according to the controlled sequence of transmission;
   an input unit for manipulating and programming the controlled sequence of transmission into the microcontroller; and
   a monitor for displaying the controlled sequence of transmission and a status of each of the plurality of electrodes.

3. The device of claim 2, wherein the stimulation control unit includes at least one interactive software program proprietary to the device, the at least one interactive software program having capability of interfacing with other third-party medical software programs.

4. The device of claim 1, wherein the stimulation control unit further comprises a neuromuscular feedback component for adjusting said FES modality according to a response in the muscles and the controlled sequence of transmission.

5. The device of claim 1, wherein the stimulation control unit further comprises a neurofeedback mechanism for adjusting said TENS modality according to an activity of nerves in the limb and the controlled sequence of transmission.

6. The device of claim 1, wherein the stimulation control unit has at least one unit fastener for removably attaching the control unit to the brace.

7. The device of claim 1, further comprising at least one conductor having a proximal end connected to the stimulation control unit and a distal end connected to at least one of the plurality of electrodes;
   wherein the at least one conductor establishes communication between the plurality of electrodes and the stimulation control unit.

8. The device of claim 1, wherein each of the plurality of electrodes and the stimulation control unit each include a transmitter-receiver unit for providing wireless communication between the stimulation control unit and the plurality of electrodes.

9. The device of claim 1, wherein each of the plurality of electrodes comprises:
   a signal generator for supplying an electrical current needed to generate one of the at least four electrophysical modalities according to the controlled sequence of transmission; and
   a fastening layer for removably attaching the electrode to an inner surface of the brace.

10. The device of claim 9, wherein each of the plurality of electrodes comprises a transmission layer adapted to receive the electrical current and transmit the at least four electrophysical modalities transcutaneously.

11. The device of claim 1, wherein the stimulation control unit further comprises a biomechanical component for monitoring and analyzing a biomechanical response and range of motion of the joint and for adjusting one or more of the at least four electrophysical modalities according the biomechanical response, range of motion, and the controlled sequence of transmission.

12. The device of claim 11, wherein the plurality of electrodes provides for the monitoring and analysis of the biomechanical response and range of motion.

13. The device of claim 11 further comprising at least one additional electrode disposed on the brace, wherein the at least one additional electrode provides for the monitoring and analysis of the biomechanical response and range of motion.

14. A non-invasive device for assisting treatment of a joint, limb, and muscles suffering from a musculoskeletal disorder, the device comprising:
   a sleeve or flexible pad adapted to fit over and conform to the joint and limb, the sleeve or flexible pad allowing for articulation of the joint and limb;
   a plurality of electrodes disposed on the sleeve or flexible pad, wherein the plurality of electrodes transmits at least the following four electrophysical modalities: neuromodulating functional electrical stimulation (FES), transcutaneous electrical nerve stimulation (TENS), pulsed electromagnetic field (PEMF) stimulation, and heat therapy stimulation;
   wherein said plurality of electrodes comprises a first group transmitting said FES modality, a second group transmitting said TENS modality, a third group transmitting said PEMF modality and a fourth group transmitting said heat therapy stimulation; and
   a stimulation control unit establishing a controlled sequence of transmission of the at least four electrophysical modalities and communicating said controlled sequence to the electrodes.

15. The device of claim 14, wherein the sleeve or flexible pad comprises an elastic material providing constant contact with the limb and joint while providing flexibility for motion of the limb and joint.

16. The device of claim 14, wherein the control unit has at least one unit fastener for removably attaching the control unit to the sleeve or flexible pad.

17. The device of claim 14, further comprising at least one conductor having a proximal end connected to the stimulation control unit and a distal end connected to at least one of the plurality of electrodes;
   wherein the at least one conductor establishes communication between the plurality of electrodes and the stimulation control unit.

18. The device of claim 14, wherein each of the plurality of electrodes and the stimulation control unit each include a transmitter-receiver unit for providing wireless communication between the stimulation control unit and the plurality of electrodes.

19. The device of claim 14, wherein:
   each of the plurality of electrodes comprises a fastening layer for removably attaching the electrode to the sleeve or flexible pad and a signal generator for supplying an electrical current needed to generate one of the at least four electrophysical modalities according to the controlled sequence of transmission.

20. The device of claim 19, wherein each of the plurality of electrodes comprises a transmission layer adapted to receive the electrical current and transmit the at least four electrophysical modalities.

21. The device of claim 20, wherein said transmission layer is in contact with an outer lining of the sleeve or flexible pad, said sleeve or flexible pad having conductive properties for providing transcutaneous transmission of the at least four electrophysical modalities from the transmission layer to the limb.

22. The device of claim 14, further comprising:
   a brace disposed without the sleeve; and
   a plurality of fasteners disposed on an outer lining of the sleeve or flexible pad, said fasteners removably attaching the sleeve or flexible pad to an inner surface of the brace;
   wherein said brace has at least one support member conforming to the limb and at least one brace fastener attached to the at least one support member and adapted to secure the at least one support member to the limb.

23. The device of claim 22, wherein the control unit has at least one unit fastener for removably attaching the control unit to the brace, sleeve, or flexible pad.

24. The device of claim 14, wherein the stimulation control unit further comprises at least one feedback component chosen from a group consisting a neuromuscular feedback component, neurofeedback mechanism, and biomechanical component, the at least one feedback component recording and analyzing a response in the limb and adjusting one or more of the least four electrophysical modalities according to said response.

25. The device of claim 24, wherein the response comprises at least one data point readout sent from at least one of the plurality of electrodes at a single time point.

26. The device of claim 24, wherein the response comprises at least one data point readout sent from at least one of the plurality of electrodes in a sequential data point progression.

27. A non-invasive device for assisting treatment of a joint, limb, and muscles suffering from a musculoskeletal disorder, the device comprising:
   a brace having at least one support member conforming to the limb and assisting movement in the limb, and at least one brace fastener, wherein the at least one brace fastener is attached to the at least one support member and is adapted to secure the at least one support member to the limb;

a sleeve or flexible pad comprising an elastic material adapted to fit over and conform to the joint and limb and allowing for articulation of the joint and limb;

a plurality of electrodes disposed on the sleeve or flexible pad, wherein the plurality of electrodes transmits a plurality of electrophysical modalities comprising all four of the following: neuromodulating functional electrical stimulation (FES), transcutaneous electrical nerve stimulation (TENS), pulsed electromagnetic field (PEMF) stimulation, and heat therapy stimulation;

wherein said plurality of electrodes comprises a first group transmitting said FES modality, a second group transmitting said TENS modality, a third group transmitting said PEMF modality and a fourth group transmitting said heat therapy stimulation; and a stimulation control unit establishing a controlled sequence of transmission of the plurality of electrophysical modalities and communicating said controlled sequence to the electrodes;

wherein the sleeve or flexible pad provides constant contact with the limb and joint while providing flexibility for motion of the limb and joint.

28. The device of claim 27, wherein the stimulation control unit has at least one unit fastener for removably attaching the control unit to the brace, sleeve, or flexible pad.

29. The device of claim 27, further comprising a plurality of fasteners disposed on the sleeve or flexible pad for removably attaching the sleeve or flexible pad to an inner surface of the brace.

30. The device of claim 27, further comprising at least one conductor having a proximal end connected to the stimulation control unit and a distal end connected to at least one of the plurality of electrodes, wherein the at least one conductor establishes communication between the plurality of electrodes and the stimulation control unit.

31. The device of claim 27, wherein each of the plurality of electrodes and the stimulation control unit each include a transmitter-receiver unit for providing wireless communication between the stimulation control unit and the plurality of electrodes.

32. The device of claim 27, wherein each of said plurality of electrodes comprises a fastening layer for removably attaching the electrode to an inner lining of the sleeve or flexible pad and a signal generator for supplying an electrical current needed to generate one of the plurality of electrophysical modalities according to the controlled sequence of transmission.

33. The device of claim 32, wherein each of the plurality of electrodes comprises a transmission layer in contact with the limb for transmitting transcutaneously the plurality of electrophysical modalities.

34. The device of claim 27, wherein each of the plurality of electrodes is capable of transmitting each of the electrophysical modalities.

35. The device of claim 27, wherein the controlled sequence comprises each of the plurality of electrodes simultaneously transmitting any one of the plurality of electrophysical modalities.

36. The device of claim 27, wherein the stimulation control unit further comprises a biomechanical component for monitoring and analyzing a biomechanical response and range of motion of the joint and for adjusting one or more of the electrophysical modalities according the biomechanical response, range of motion, and the controlled sequence of transmission.

37. A non-invasive device for assisting treatment of a joint, limb, and muscles suffering from a musculoskeletal disorder, the device comprising:

a brace having at least one support member conforming to the limb and assisting movement in the limb, and at least one brace fastener, wherein the at least one brace fastener is attached to the at least one support member and is adapted to secure the at least one support member to the limb;

a sleeve comprising an elastic material adapted to fit over and conform to the joint and limb and assisting movement in the joint and limb;

at least one flexible pad comprising a material adapted to conform to and accommodate anatomical aspects of the joint and limb and allowing for articulation of the joint and limb;

a plurality of electrodes disposed on the sleeve and the at least one flexible pad, wherein the plurality of electrodes transmits a plurality of electrophysical modalities comprising the following: neuromodulating functional electrical stimulation (FES), transcutaneous electrical nerve stimulation (TENS), pulsed electromagnetic field (PEMF) stimulation, and heat therapy stimulation;

wherein said plurality of electrodes comprises a first group transmitting said FES modality, a second group transmitting said TENS modality, a third group transmitting said PEMF modality and a fourth group transmitting said heat therapy stimulation;

a stimulation control unit establishing a controlled sequence of transmission of the plurality of electrophysical modalities and communicating said controlled sequence to the electrodes;

wherein the sleeve and the at least one flexible pad provide constant contact with the limb and joint while providing flexibility for motion of the limb and joint; and wherein the stimulation control unit further provides for monitoring and analysis of biomechanical response and range of motion of the limb.

38. The device of claim 37, wherein the brace, sleeve and pad have marking features for promoting substantially identical positioning of the brace, sleeve and pad with respect to the limb from one treatment session to another treatment session.

* * * * *